United States Patent [19]
Adamus et al.

[11] Patent Number: 5,599,817
[45] Date of Patent: Feb. 4, 1997

[54] XANTHINE DERIVATIVES AS DIURETIC AGENTS

[75] Inventors: Stefan Adamus; Wolfram Gaida, both of Ingelheim; Christopher Meade, Bingen-Büdesheim; Ulrike Küfner-Muhl, Ingelheim, all of Germany

[73] Assignee: Boehringer Ingelheim KG, Ingelheim am Rhein, Germany

[21] Appl. No.: 436,220

[22] PCT Filed: Nov. 11, 1993

[86] PCT No.: PCT/EP93/03158

§ 371 Date: Jul. 6, 1995

§ 102(e) Date: Jul. 6, 1995

[87] PCT Pub. No.: WO94/11000

PCT Pub. Date: May 26, 1994

[30] Foreign Application Priority Data

Nov. 13, 1992 [DE] Germany ............ 42 38 367.6

[51] Int. Cl.$^6$ .......... A61K 31/19; A61K 31/34; A61K 31/52
[52] U.S. Cl. .......... 514/263; 514/568; 514/471; 514/562
[58] Field of Search .......... 514/265, 263, 514/255, 234.2, 471, 562, 568

[56] References Cited

U.S. PATENT DOCUMENTS 3,624,215  11/1971  Stein ............ 424/253
4,755,517   7/1988  Bruns ............ 514/263

FOREIGN PATENT DOCUMENTS 1201997  8/1970  United Kingdom.

OTHER PUBLICATIONS

Suzuki et al., J. Med. Chem., 35(16), 3066–75 (1992).
*Chemical Abstracts* vol. No. 88, No. 21, Abstract No. 152567v (1978).
*Chemical Abstracts*, vol. No. 106, No. 19, Abstract No. 149315w (1987).
*Chemical Abstracts*, vol. No. 107, No. 1, p. 18, Abstract No. 259u (1987).
*Chemical Abstracts*, vol. No. 108, No. 11, p. 658, Abstract No. 94512s (1988).
*Chemical Abstracts*, vol. No. 109, No. 15, p. 106, Abstract No. 122899q (1988).
*Chemical Abstracts*, vol. No. 109, No. 25, Abstract No. 221931a (1988).
A. Erndt et al., "Photoreactions of Theophylline with Ethers in the Presence of Aliphatic Ketones", *Liebigs Ann. Chem.*, pp. 937–943 (1985).

*Primary Examiner*—Phyllis G. Spivack
*Attorney, Agent, or Firm*—Robert P. Raymond; Wendy E. Rieder; Alan R. Stempel

[57] ABSTRACT

A method for stimulating diuresis comprising administering a composition comprising 8-(3-oxocyclopentyl)-1,3-di-n-propyl-7H-purine-2,6-dione and, optionally, a loop diuretic, is disclosed.

3 Claims, No Drawings

XANTHINE DERIVATIVES AS DIURETIC AGENTS

This application is a '371 of PCT/EP93/03158 filed Oct. 11, 1993.

The present invention relates to the use of 8-(3-oxocyclopentyl)-1,3-dipropyl-7H-purine-2,6-dione and xanthines of similar structure as diuretics. Diuretics play an important part in the treatment of oedema, hypertension and other illnesses.

The diuretic effect of xanthines is known in principle, but the compounds investigated hitherto have a relatively weak activity (see Beutler J. J., Koomans H. A., Bijlsma J. A. Dorhout-Mees E. J., J. Pharmacol. exp. Ther. (1990) 255, 1314).

Surprisingly, it has now been found that 8-(3oxocyclopentyl)-1,3 -dipropyl-7H-purine-2,6-dione (KFM 19) is an extremely effective diuretic. A significant diuretic effect is observed at an oral dose of only 0.03 mg/kg of body weight (in the rat). Particular advantages are expected from combining the substances of this application with so-called loop diuretics such as furosemide, bumetanide and ethacrynic acid. The "loop diuretics" are highly effective substances which inhibit the transporting of sodium in the distal tubuli of the kidneys. At the same time, chloride resorption is inhibited (NACl co-transport) (Imai M, Eur. J. Pharmacol. (1977) 41, 409). 8-(3-Oxocyclopentyl)-1,3-dipropyl-7H-purine-2,6-dione increases the excretion of sodium and chloride without having any great effect on potassium excretion. It is known that adenosine can influence chloride secretion. Therefore it is probable that the diuretic mechanisms of activity mainly affect the transport of chloride ions and the substance works in a complementary manner with agents inhibiting sodium chloride resorption.

DESCRIPTION OF THE TEST PROCEDURE

The tests were carried out with conscious male rats (Chbb:THOM, SPF) weighing 240–280 g which had been fasting. 10 animals were used for each dose, with two animals in each metabolic cage (n=5). In order to stimulate diuresis, all the animals were given water by oral route in an amount of 5 ml/100 g of body weight by oesophageal tube. KFM 19 was dissolved in water and administered orally together with the water (1 ml solution, 4 ml water) by oesophageal tube in doses of 0.01, 0.03, 0.1 and 0.3 mg/kg. The control animals were given 5 ml of water. Two and five hours after administration, the volume of urine excreted was measured; the sodium and potassium contents were determined by flame photometry and the chloride content by mercurimetry.

The results were checked for statistical significance according to DUNNETT (1984).

Table I

Influence on the excretion of urine and electrolyte of the oral administration of 8-(3-oxocyclopentyl)-1,3-dipropyl-7H-purine-2,6-dione in five hours after administration

| Dose mg/kg p.o. | Volume of urine ml/100 g x ± Sx | Sodium uVal/100 g x ± Sx | Potassium uVal/100 g x ± Sx | Chloride uVal 100 g x ± Sx |
|---|---|---|---|---|
| Control | 3.9 ± 0.5 | 32.3 ± 8.4 | 68.0 ± 13.9 | 65.2 ± 10.7 |
| 0.01 | 4.7 ± 0.3 | 45.9 ± 7.0 | 101.1 ± 14.6 | 88.5 ± 10.1 |
| 0.03 | 4.1 ± 0.4 | 51.7 ± 6.6 | 85.4 ± 4.4 | 87.0 ± 8.1 |
| 0.1 | 5.1 ± 0.2* | 81.1 ± 8.1* | 101.3 ± 9.1 | 138.5 ± 14.0** |
| 0.3 | 5.8 ± 0.2** | 131.5 ± 10.0** | 119.8 ± 8.4 | 174.1 ± 18.5** |

\* = p < 0.05,
\*\* = p < 0.01

In the light of these findings, the above-mentioned compound as well as the structurally similar compounds appear to be suitable as diuretics, particularly for the treatment of oedema, hypertension and other indications of this kind.

Suitable xanthine derivatives of similar structure are described in European Patent Applications 374 808 and 487 673, to which reference is expressly made, particularly the ranges and embodiments described by way of example as being preferred.

These compounds may also be used for treating illnesses caused by disrupted transport of chloride ions.

Xanthines of general formula

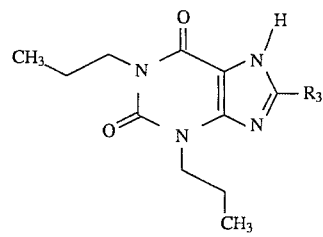

are therefore also of interest, wherein $R_3$ denotes a group selected from among furan, tetrahydrofuran, tetrahydrofuranone, thiophene and dithiole, dithiane or tetrahydropyran which may carry one of the following substituents: methyl, ethyl, propyl, butyl, CHO, $CH_2OR_4$, $CH_2OR_7$, $COOR_4$, $CONR_5R_6$, $R_3$ denotes a furan substituted by —CH=CH—$CONR_5BR_6$,    —CH=C$(COOR_4)_2$
  (wherein $R_4$ may be identical or different),

—CH=C—$(COOR_4)$—( $CONR_5R_6$),

—CH=C $(COOR_4)$ $(CH_2OR_4)$ (wherein $R_4$ may be identical or different),

—CH=C $(COOR_4)$ $(CH_2OR_7)$,

—$(CH_2)_n$—$CONR_5R_6$,

—CH=C $(CH_2OR_4)_2$,

—CH=C $(CH_2OR_7)_2$,

—CH=C $(CONR_5R_6)CH_2OR_4$ or

—CH=C $(CONR_5R_6)CH_2OR_7$;

$R_3$ denotes a cyclopentane or cyclohexane substituted by methyl, ethyl, propyl, iso-propyl, t-butyl, allyl, vinyl, phenyl or benzyl, whilst a hydroxy group may be present as a geminal substituent;

$R_3$ denotes a cyclopentane or cyclohexane substituted by hydroxy, methoxy, ethoxy, propyloxy, trimethoxycarbonyl, iso-propyloxy, optionally substituted benzyloxy, allyloxy, propargyloxy, —$CH_2$—CO—$OCH_3$, =C—CO—$OCH_3$, —$CH_2$—$CH_2$—OH, —$CH_2$—$COOCH_3$, =CH—$COOCH_3$, $CH_2$—$CH_2$—OH, =CH—CN, —$(CH_2)_2NH_2$=$CH_2$,

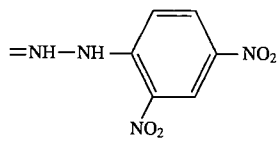

=NOH, —$CH_2OH$, $OR_4$ wherein $R_4$=methyl or trityl, $OR_7$ wherein $R_7$ denotes $COCH_3$, $COC_2H_5$, $COC_3H_7$, CO t-butyl, —CO-phenyl or $COCH_2$-phenyl, optionally substituted, CO-pyridyl, —CO—(N-methyl-4H-pyridyl), —CO—(methylpyridyl), —$COCH_2$—CH=$CH_2$, —CO $CH_2$—C≡CH;

$R_3$ denotes a group

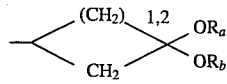

wherein $R_a$, $R_b$=$CH_3$, $C_2H_5$ or $R_a$ and $R_b$ together denote —$CH_2$—$CH_2$—, $R_3$ denotes a cyclopentanone or cyclohexanone, $R_3$ denotes a cycloalkane or cycloalkene having 4 to 8 carbon atoms which may optionally be substituted by a straight-chained or branched $C_{2-4}$-alkenyl group, or a cyclopentanone or cyclopentanol or cyclohexanone or cyclohexanol which may be substituted in the α-position relative to the keto- or hydroxy group by $C_{2-4}$-alkenyl, $C_3$ or $C_4$-alkynyl, benzyl, —$CH_2CH_2CN$, $(CH_2)_3NR_5R_5$ (wherein $R_5$ may be identical or different), $CH_2COOR_4$ or $CH_2OR_4$, wherein $R_4$ may denote hydrogen, methyl, ethyl or propyl;

$R_3$ denotes norbornane or norbornene- optionally substituted,

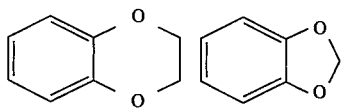

$R_4$ denotes hydrogen, a $C_{1-3}$-alkyl group, a cyclopropyl group, a cyclopentyl group, benzyl an allyl group, a propargyl group, a triphenylmethyl group;

$R_5$ denotes hydrogen, a $C_{1-3}$-alkyl group; a cyclopropyl group, a benzyl group;

$R_6$ denotes hydrogen, methyl, ethyl, propyl, —$(CH_2)_n$—$NH_2$ (n=2-8), —$(CH_2)_nNEt_2$ (n=2,3) or —$(CH_2)_3$—O—$(CH_2)_4$—O—$(CH_2)_3$—$NH_2$, N-benzyl-piperidin-4-yl, or $R_5$ and $R_6$ together with the nitrogen atom denote a piperidine, piperazine or morpholine group which may optionally be substituted by a $C_{1-4}$-alkyl group, preferably methyl;

$R_7$ denotes prolinoyl, CO—$(CH_2)_{0-3}$—$CH_3$, (—)—menthoxy-acetyl, a camphanic acid group linked via a carbonyl group, an abietinoyl, benzoyl, 4-aminobutyroyl, 3,4,5-trihydroxybenzoyl, 3,4,5-trimethoxybenzoyl, a nicotinic acid, isonicotinic acid or picolinic acid group, N-methylnicotinic acid group, N-methyl-4H-nicotinic acid group, and optionally the acid addition salts thereof.

In this connection the use of 8-(3-oxocyclopentyl)-1,3-di-n-propyl-7H-purine-2,6-dione or one of its enantiomers (+)-8-(3-oxocyclopentyl)-1,3-di-n-propyl-7H-purine-2,6-dione or (−)-8-(3-oxocyclopentyl)-1,3-di-n-propyl-7H-purine-2,6-dione as a diuretic is of particular interest.

It is also advantageous to use 8-(3-hydroxycyclopentyl)-1,3-di-n-propyl-7H-purine-2,6-dione or the enantiomers thereof as a diuretic.

The present invention further relates to the combination of compounds of general formula I, particularly the compounds mentioned by name, with loop diuretics such as furosemide, bumetamide and ethacrynic acid.

The compounds of general formula I can be administered orally or parenterally or in suppository form. The compounds are present as active ingredients in conventional pharmaceutical preparations, e.g. in compositions consisting essentially of an inert pharmaceutical carrier and an effective dose of the active substance, such as plain or coated tablets, capsules, lozenges, powders, solutions, suspensions, emulsions, elixirs, suppositories and so on. An effective dose of the compounds, for the indication claimed according to the invention, is between 5 and 100 mg per dose, preferably between 10 and 50 mg, for oral administration.

We claim:

1. A method for stimulating diuresis comprising the step of administering to a patient an effective amount of a pharmaceutical composition comprising 8-(3-oxocyclopentyl)-1,3-di-n-propyl-7H-purine-2,6-dione or an enantiomer thereof and an inert pharmaceutical carrier.

2. The method according to claim 1, wherein said pharmaceutical composition further comprises a loop diuretic.

3. The method according to claim 2, wherein the loop diuretic is selected from the group consisting of furosemide, bumetanide or ethacrynic acid.

* * * * *